(12) United States Patent
Shinozaki et al.

(10) Patent No.: US 8,691,886 B2
(45) Date of Patent: Apr. 8, 2014

(54) DENTAL HYDRAULIC TEMPORARY SEALING MATERIAL COMPOSITION

(75) Inventors: Yutaka Shinozaki, Itabashi-ku (JP);
Shouichi Fukushima, Itabashi-ku (JP);
Hiroshi Kamohara, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/075,516

(22) Filed: Mar. 30, 2011

(65) Prior Publication Data

US 2011/0244431 A1 Oct. 6, 2011

(30) Foreign Application Priority Data

Mar. 31, 2010 (JP) ................... 2010-080845

(51) Int. Cl.
*A61K 6/08* (2006.01)
(52) U.S. Cl.
USPC .......... 523/116; 523/117; 433/106; 433/226; 433/228.1
(58) Field of Classification Search
USPC ............... 433/106, 226, 228.1; 523/116, 117
See application file for complete search history.

(56) References Cited

U.S. PATENT DOCUMENTS

2002/0197214 A1* 12/2002 Bublewitz et al. ............. 424/53
2004/0028624 A1* 2/2004 Bublewitz et al. ............. 424/53

FOREIGN PATENT DOCUMENTS

| JP | S38-2628 | 3/1963 | |
| JP | 04-317656 | 11/1992 | |
| JP | 04317656 A | * 11/1992 | |
| JP | 04317656 A | * 11/1992 | |
| JP | 10-87419 | 4/1998 | |
| KR | 2002-0035727 | 5/2002 | |
| KR | 20020035727 A | * 5/2002 | ............... A61K 6/02 |

OTHER PUBLICATIONS

Menthanol MSDS, Natural Sourcing,Oxford,CT., Jan. 1, 2008.*
Generally Recognized as Safe (GRAS) Notification for Glycerol Ester of Gum Rosin, Environ Int'l Corp, Jun. 24, 2002.*
Extended European Search Report issued Sep. 7, 2011, in Patent Application No. 11002468.4.

* cited by examiner

*Primary Examiner* — James J Seidleck
*Assistant Examiner* — Peter A Salamon
(74) *Attorney, Agent, or Firm* — Oblon, Spivak, McClelland, Maier & Neustadt, L.L.P.

(57) ABSTRACT

To provide a dental hydraulic temporary sealing material composition setting faster than conventional composition, excellent adhesiveness with cavity, and extremely good operativity of filling in an oral cavity, the dental hydraulic temporary sealing material composition includes calcium sulfate, a vinyl acetate resin, an inorganic filler, alcohols having a boiling point of 110° C. or more, and a nonionic surfactant, whereby water on a cavity can adhere, without being repelled, to a paste surface due to hydrophilic effect between an organic solvent having proper hydrophilicity and the nonionic surfactant, the water can permeate and diffuse rapidly and stably through the inside of the paste by the hydrophilic effect so as to set faster than conventional composition, and since the hydrophilic effect is effective for adhesiveness with cavity, filling property in an oral cavity becomes extremely good.

12 Claims, No Drawings

DENTAL HYDRAULIC TEMPORARY SEALING MATERIAL COMPOSITION

BACKGROUND OF THE INVENTION

1. Field of the Invention

The present invention relates to a dental hydraulic temporary sealing material composition used as a temporary sealing material in dental treatments.

2. Description of the Conventional Art

In dental treatments, temporary sealing for sealing a cavity for a fixed period of time has been performed for follow-up observation until a next visit to a dental clinic, prevention of food piece insertion and bacterial infection into a cavity until a dental crown product is produced after forming the cavity, prevention of leakage of a medicament filled in a cavity or a root canal, and the like. The dental temporary sealing material means a material used for such the temporary sealing.

As for the characteristics of the dental temporary sealing material, the material has a closely sealing effect, can resist occlusal pressure so as not to be broken, fallen, and deformed, is not harmful to hard tissue of a tooth and a pulp, can be easily operated to be filled and removed, and the like. The dental temporary sealing material can be roughly classified into three kinds, i.e., thermoplastic resins (a temporary stopping), dental cements (an eugenol cement, a non-eugenol cement, a zinc phosphate cement), and hydraulic temporary sealing materials.

Since the thermoplastic resin (temporary stopping) is formed in a rod shape or a pellet shape and supplied, the thermoplastic resin is used by being heated/softened and pressed to contact with the cavity. The thermoplastic resin has been widely used because filling and removing operations are easy. However, since the shrinkage of thermoplastic resin is large at a time of being cooled/cured, adhesiveness between the thermoplastic resin and a cavity is not enough, so that the thermoplastic resin does not have sufficient sealing property for the cavity. Further, since the thermoplastic resin needs heating/softening at a time of filling, flame and the like are certainly required when the thermoplastic resin is operated, so that the operation for the thermoplastic resin is complicated.

Further, the dental cements (an eugenol cement, a non-eugenol cement, and a zinc phosphate cement) are filled after being mixed powders and liquids to be a paste state. Since these dental cements become a set material with proper hardness in several minutes, these dental cements have excellent sealing property for the cavity, and may have effects of sedation, analgesia and antimicrobial activity. However, the mixing operation of powders and liquids is complicated and needs skillfulness. Further, there is a fault that a removing operation is difficult because the set material is comparatively hard. Furthermore, the eugenol cement has problems of a peculiar odor and stimulation to mucosal tissue.

The hydraulic temporary sealing material does not have adhesiveness with cavity, but when a putty-like paste is filled in the cavity, the paste reacts with water such as saliva in an oral cavity and is set. Therefore, the hydraulic temporary sealing material does not need mixing/heating, and has good operativity. Further, the hydraulic temporary sealing material has good sealing property because it expands at a time of setting (e.g., refer to Japanese Patent No. S38-2628). However, since the hydraulic temporary sealing material utilizes a setting mechanism due to the reaction of calcium sulfate in a composition with the water in the oral cavity, there are problems that a setting time is long and the initial setting time is particularly slow.

SUMMARY OF THE INVENTION

Problems to be Solved by the Invention

An objective of the present invention is to provide a dental hydraulic temporary sealing material composition which sets faster than a conventional composition, high sealing property, and very good operativity of filling in an oral cavity.

Means for Solving the Problem

Present inventors carried out earnest works to solve the aforementioned problems, and as a result, they found out the followings to complete the present invention. When, a dental hydraulic temporary sealing material composition consists of calcium sulfate, a vinyl acetate resin, an inorganic filler, alcohols having a boiling point of 110° C. or more, and a nonionic surfactant, water on a cavity can adhere, without being repelled, to a paste surface due to hydrophilic effect between an organic solvent having proper hydrophilicity and the nonionic surfactant. The water can permeate and diffuse rapidly and stably through the inside of the paste by the hydrophilic effect so as to set faster than conventional composition. Furthermore, since the hydrophilic effect is effective for adhesiveness with cavity, filling property in an oral cavity becomes good. As a result, the sealing property can be improved.

More specifically, according to an aspect of the present invention, a dental hydraulic temporary sealing material composition includes A) 10 to 90% by weight of calcium sulfate, B) 5 to 40% by weight of a vinyl acetate resin, C) 1 to 40% by weight of an inorganic filler, D) 1 to 30% by weight of alcohols having a boiling point of 110° C. or more, and E) 0.001 to 5% by weight of a nonionic surfactant.

Effect of the Invention

The dental hydraulic temporary sealing material composition according to the present invention is a dental hydraulic temporary sealing material composition set faster setting than conventional composition, high sealing property, and very good operativity of filling in an oral cavity.

DETAILED DESCRIPTION OF PREFERRED EMBODIMENT

A dental hydraulic temporary sealing material composition according to the present invention is a dental hydraulic temporary sealing material consisting of A) 10 to 90% by weight of calcium sulfate, B) 5 to 40% by weight of a vinyl acetate resin, C) 1 to 40% by weight of an inorganic filler, D) 1 to 30% by weight of alcohols having a boiling point of 110° C. or more, and E) 0.001 to 5% by weight of a nonionic surfactant.

The A) component is calcium sulfate and the component which gives the strength of the material together with giving a basic setting mechanism as the dental hydraulic temporary sealing material. The A) component is set by reaction of calcium sulfate with the water such as saliva.

The content of calcium sulfate as the A) component needs to be 10 to 90% by weight in the dental hydraulic temporary sealing material composition. If the content is less than 10% by weight, a required setting reaction cannot be given to the dental hydraulic temporary sealing material composition, and the strength becomes insufficient. If the content exceeds 90% by weight, a paste before setting becomes hard too much, and the filling operation for cavity becomes difficult. Specifically, if the content is within a range from 30 to 70% by weight, the dental hydraulic temporary sealing material composition can show sufficient setting reaction and have proper adhesiveness and strength, so that it is preferable. Examples of calcium sulfate can be α-type hemihydrate gypsum, β-type hemihydrate gypsum, gypsum dihydrate, anhydrous gypsum and the like. These calcium sulfates can be used by mixing two or more kinds.

The vinyl acetate resin as the B) component is blended as a base material for giving plasticity to the dental hydraulic temporary sealing material composition. Further, using of the vinyl acetate resin together with a D) component described below can increase adhesiveness to a dentine. Examples of the vinyl acetate resin can be polyvinyl acetate, an ethylene vinyl acetate copolymer, a copolymer of vinyl acetate and vinyl chloride, a copolymer of vinyl acetate and acrylonitrile, a copolymer of vinyl ester and vinyl chloride, acrylic acid, maleic acid, fumaric acid, crotonic acid, a copolymer of these acids and ester, and the like. These can be used by mixing two or more kinds.

The blending amount of the B) component needs to be 5 to 40% by weight in the dental hydraulic temporary sealing material composition. If the blending amount is less than 5% by weight, the dental hydraulic temporary sealing material composition cannot have plasticity required, and formability and filling operativity decrease. If the blending amount exceeds 40% by weight, strength decreases, the composition adheres to a filling instrument too much, so that filling operativity to cavity decreases. Specifically, if the amount is within a range from 10 to 30% by weight, a proper formability and filling operativity can be obtained, so that it is preferable.

The inorganic filler as the C) component gives strength to the dental hydraulic temporary sealing material composition. As for the inorganic filler, for example, zinc oxide, silica, silica fine powder, barium sulfate, zirconium oxide, titanium oxide, ytterbium fluoride, barium glass and aluminosilicate glass can be used. The content of the inorganic filler is 1 to 40% by weight. If the content is less than 1% by weight, the strength decreases, and the formability of the dental hydraulic temporary sealing material composition becomes insufficient. If the content exceeds 40% by weight, the composition becomes fragile. Specifically, if the content is within a range from 10 to 30% by weight, the strength is proper, so that it is preferable.

The alcohols having a boiling point of 110° C. or more as the D) component are a component for making the dental hydraulic temporary sealing material composition to be pasty. The component is also to set faster than conventional dental hydraulic temporary sealing material. By adding of an organic solvent having proper hydrophilicity to the dental hydraulic temporary sealing material composition, hydrophilic effect can be obtained, so that water can permeate more rapidly without being repelled on the paste surface, and can rapidly and stably permeate and diffuse inside the paste. Therefore, a water absorption rate is improved, and the initial setting is improved. The effect of the D) component can be more improved by using the alcohols together with the E) component described below.

As for the alcohols as the D) component, any of alcohols including one hydroxyl group and polyhydric alcohols including two or more hydroxyl groups can be used without limitation if these alcohols have a boiling point of 110° C. or more. Examples of preferable alcohols can be 1-butanol, t-butyl alcohol, 1-pentanol, isoamyl alcohol, s-amyl alcohol, t-amyl alcohol, 1-hexanol, 2-ethyl-1-butanol, 4-methyl-2-pentanol, isohexyl alcohol, methyl-1-pentanol, s-hexanol, 1-heptanol, isoheptyl alcohol, 2,3-dimethyl-1-pentanol, 1-octanol, 2-ethyl hexanol, isooctyl alcohol, 2-octanol, 3-octanol, 1-nonanol, isononyl alcohol, 3,5,5-trimethylhexanol, 1-decanol, isodecyl alcohol, 3,7-dimethyl-1-octanol, 1-dodecanol, isododecyl alcohol, higher alcohol having 6 to 11 carbons, ethylene glycol, triethylene glycol, tetraethylene glycol, polyethylene glycol, propylene glycol, 1,3 propanediol, dipropylene glycol, tripropylene glycol, polypropylene glycol, butanediol, 1,5-pentanediol, 2-methyl-2,4 pentanediol, 2,2,4-trimethyl-1,3-hexanediol, 2-ethyl-1,3-hexanediol, ethylene glycol monomethyl ether, ethylene glycol monovinyl ether, ethylene glycol monoethyl ether, ethylene glycol mono-n-propyl ether, ethylene glycol monoisopropyl ether, ethylene glycol mono-n-butyl ether, ethylene glycol monoisobutyl ether, ethylene glycol mono-t-butyl ether, ethylene glycol mono-2-methylpentyl ether, ethylene glycol mono-n-hexyl ether, ethylene glycol mono-2,4-hexadiene ether, ethylene glycol mono-2,6,8-trimethyl-4-nonyl ether, ethylene glycol monophenyl ether, ethylene glycol monomethylphenyl ether, ethylene glycol dimethyl ether, ethylene glycol diethyl ether, diethylene glycol monomethyl ether, diethylene glycol monoethyl ether, diethylene glycol mono-n-propyl ether, diethylene glycol mono-n-butyl ether, diethylene glycol monoisobutyl ether, diethylene glycol mono-n-hexyl ether, diethylene glycol dimethyl ether, diethylene glycol divinyl ether, diethylene glycol ethylvinyl ether, diethylene glycol monomethylphenyl ether, triethylene glycol monomethyl ether, triethylene glycol monoethyl ether, triethylene glycol mono-n-propyl ether, triethylene glycol monovinylethyl ether, tetraethylene glycol methyl ether, tetraethylene glycol butyl ether, tetraethylene glycol monophenyl ether, tetraethylene glycol diethyl ether, polyethylene glycol methyl ether, propylene glycol monomethyl ether, propylene glycol monoethyl ether, propylene glycol-n-monopropyl ether, propylene glycol monoisopropyl ether, propylene glycol mono-n-butyl ether, propylene glycol butoxyethyl ether, propylene glycol phenyl ether, dipropylene glycol monomethyl ether, dipropylene glycol monoethyl ether, dipropylene glycol mono-n-butyl ether, propylene glycol allyl ether, dipropylene glycol allyl ether, tripropylene glycol allyl ether, propylene glycol isobutyl ether, dipropylene glycol isobutyl ether, tripropylene glycol isobutyl ether, butylene glycol monomethyl ether, butylene glycol monoethyl ether, butylene glycol mono-n-butyl ether, and the like. These alcohols can be used by mixing two or more kinds.

The blending amount of the D) component is 1 to 30% by weight in the dental hydraulic temporary sealing material composition. If the blending amount is less than 1% by weight, the hydrophilic effect is not enough, and a paste state required for the dental hydraulic temporary sealing material composition cannot be made, so that the filling operativity decreases. If the blending amount exceeds 30% by weight, a setting speed becomes low, so that the initial setting decreases. Specifically, if the blending amount is within a range from 2 to 20% by weight, the proper setting can be obtained, and the filling operativity becomes the best. So, it is preferable.

The nonionic surfactant which is the E) component increases compatibility with water, and sets faster than conventional composition by use of it together with the above-described D) component. As the nonionic surfactant used as the E) component, a nonionic surfactant having combination of a hydrophilic group with an alkyl group which is a lipophilic group is proper. Specific examples of the preferable nonionic surfactant can be agents having 1 to 30 addition molar number of ethylene oxide or propylene oxide among polyoxyethylene alkyl ether, polyoxyethylene alkylene ether, polyoxyethylene polyoxypropylene alkyl ether, polyoxyethylene alkylphenyl ether and the like, ether-type agents having 12 to 22 carbons in a alkyl group, partial ester type agents of polyhydric alcohol and fatty acid having 12 to 22 carbons among sorbitan fatty acid ester, glycerine fatty acid ester, polyglycerine fatty acid ester, ethylene glycol fatty acid ester, polyethylene glycol fatty acid ester, propylene glycol fatty acid ester, pentaerythritol fatty acid ester and the like, ether ester type agents having 1 to 30 addition molar number of ethylene oxide and with fatty acid having 12 to 22 carbons among polyoxyethylene sorbitan fatty acid ester, polyoxyethylene sorbit fatty acid ester, polyoxyethylene mannitan fatty acid ester, polyoxyethylene glycerine fatty acid ester, polyoxyethylene propylene glycol mono fatty acid ester and the like, or ester type agents having 1 to 30 addition molar number of ethylene oxide among a polyoxyethylene castor oil, a hardened castor oil, a polyoxyethylene lanoline derivative, a polyoxyethylene beeswax derivative and the like. These nonionic surfactants can be used by mixing two or more kinds.

The blending amount of the E) component is 0.001 to 5% by weight in the dental hydraulic temporary sealing material composition. If the blending amount is less than 0.001% by weight, the hydrophilic effect is not enough. On the other hand, if the blending amount exceeds 5% by weight, storage stability of the dental hydraulic temporary sealing material composition decreases. Specifically, if the blending amount is within a range from 0.01 to 2% by weight, the storage stability can be obtained and the hydrophilicity can be proper, so that it is preferable.

In addition, the dental hydraulic temporary sealing material composition according to the present invention at least includes the above A) to E) components and can include other arbitrary components if these components do not damage the objective of the present invention. The arbitrary components can be setting accelerators such as hydrochloride, sulfate, and the like, oily components such as hydrocarbons, higher fatty acids, esters, and the like, various kinds of inorganic or organic coloring agents, antibacterial materials, perfumes, and the like.

EXAMPLE

Dental hydraulic temporary sealing material compositions used for each example and comparative example were produced by weighing each of the components according to the blending amounts shown in Table 1 and kneading the components by a kneading device. In addition, a conventional dental hydraulic temporary sealing material composition (product name: GC CAVITON, produced by GC Corporation) was used for comparative example 3.

[Initial Hardness]

In order to evaluate initial setting of the dental hydraulic temporary sealing material composition, the dental hydraulic temporary sealing material composition was filled in a metal ring having a diameter φ of 10 mm and a height of 5 mm, and dipped in water at 37° C. for one hour. Then, a surface strength of a testing piece was measured by mounting a needle of two (vicat needle) having a cross section of 1 mm$^2$ on a universal testing machine (product name: AUTOGRAPH AG-IS, produced by Shimazu Corporation) and penetrating the needle at a crosshead speed of 1 mm/min.

[Evaluation of Operativity]

In order to evaluate operativity of the dental hydraulic temporary sealing material composition, a cavity having a diameter of about 3 mm and a depth of about 2 mm was formed in a cow's tooth, and the dental hydraulic temporary sealing material composition was filled in the cavity with a dental instrument. The operativity at a time of filling was evaluated with the following criterion.

Good: The dental hydraulic temporary sealing material composition could be filled, without adhering to the dental instrument.

Average: The dental hydraulic temporary sealing material composition could be filled although adhering to the dental instrument.

Poor: The dental hydraulic temporary sealing material composition adhered to the dental instrument and could not be filled to cavity.

[Evaluation of Adhesiveness]

In order to evaluate adhesiveness, the dental hydraulic temporary sealing material composition shown in each example and each comparative example were filled to a root canal, which was obtained by expanding a root canal of a tooth root model (product name: Tooth Root Canal Model, produced by Nissinsha Corporation), with a dental instrument. Then, the adhesiveness was evaluated. As for the evaluation, "Good" shows a case that the composition could closely adhere to a root canal wall, without forming a space, and "Poor" shows a case that the composition adhered having a slight space.

TABLE 1

| Components | | | Example 1 | Example 2 | Example 3 | Example 4 | Comparative example 1 | Comparative example 2 | Comparative example 3 |
|---|---|---|---|---|---|---|---|---|---|
| A | Calcium sulfates | aa-type hemihydrate gypsum | | 58 | | 40 | | 58 | GC CAVITON |
| | | bb-type hemihydrate gypsum | 32 | | 38 | 20 | 39 | | |
| | | Gypsum dihydrate | | | 10 | | | | |
| | | Anhydrous gypsum | | | | 5 | | | |
| B | Vinyl acetate resins | Polyvinyl acetate | 8 | | 15 | | 3 | | |
| | | Ethylene vinyl acetate copolymer | | 20 | | | | 20 | |
| | | Copolymer of vinyl acetate and vinyl chloride | 20 | | | | | | |
| | | Copolymer of vinyl acetate and acrylic ester | | | | 10 | | | |
| C | Inorganic fillers | Zinc oxide | 10 | | 28 | | 10 | | |
| | | Silica fine powders | 6 | | | | 6 | | |
| | | Barium sulfate | | 10 | | | | 10 | |
| | | Silica | | | | 18 | | | |

TABLE 1-continued

| Components | | | Example 1 | Example 2 | Example 3 | Example 4 | Comparative example 1 | Comparative example 2 | Comparative example 3 |
|---|---|---|---|---|---|---|---|---|---|
| D | Alcohols having a boiling point of 110° C. or more | 2-ethyl hexanol | 3 | | | | 8 | | |
| | | Propylene glycol | | | | 4 | | | |
| | | Diethylene glycol monoethyl ether | 15 | 10 | | | 30 | | |
| | | Dipropylene glycol n btyl ether | | | 7 | | | | |
| | Organic sovent being not the D component | Ethanol | | | | | | 10 | |
| E | Nonionic surfactants | Polyoxyethylene alkyl ether | 0.5 | 1 | | | 0.5 | 1 | |
| | | Polyoxyethylene alkylphenyl ether | | | 0.05 | | | | |
| | | Glycerine fatty acid ester | | 1 | | 1 | | 1 | |
| | Others | Sodium chloride | | | 0.9 | | 3 | | |
| | | Zinc sulfate | 5 | | | | | | |
| | | Red iron oxide | 0.5 | | 1 | 1 | 0.5 | | |
| | | Perfume | | | 0.05 | | | | |
| | | Lanolin | | | | 1 | | | |
| Total | | | 100 | 100 | 100 | 100 | 100 | 100 | |
| Initial hardening strength | | | 3.2N | 3.5N | 2.8N | 3.3N | 1.6N | 1.5N | 1.8N |
| Operativity | | | Good | Good | Good | Good | Poor | Average | Average |
| Adhesiveness | | | Good | Good | Good | Good | Poor | Poor | Poor |

Clearly from Table 1, it was confirmed that the dental hydraulic temporary sealing material compositions according to the present invention shown in examples sets faster, operativity and adhesiveness than comparative examples 1, 2 and 3.

What is claimed is:

1. A dental hydraulic temporary sealing material composition comprising:
   A) 10 to 90% by weight of calcium sulfate;
   B) 5 to 40% by weight of a vinyl acetate resin;
   C) 1 to 40% by weight of an inorganic filler;
   D) 1 to 30% by weight of at least one alcohol having a boiling point of 110° C. or more; and
   E) 0.001 to 2% by weight of a nonionic surfactant, wherein the nonionic surfactant is selected from the group consisting of polyoxyethylene alkyl ether, polyoxyethylene alkylene ether, polyoxyethylene polyoxypropylene alkyl ether, polyoxyethylene alkylphenyl ether, sorbitan fatty acid ester, ethylene glycol fatty acid ester, polyethylene glycol fatty acid ester, propylene glycol fatty acid ester, pentaerythritol fatty acid ester, polyoxyethylene sorbitan fatty acid ester, polyoxyethylene sorbital fatty acid ester, polyoxyethylene mannitan fatty acid ester, polyoxyethylene glycerine fatty acid ester, polyoxyethylene propylene glycol mono fatty acid, polyoxyethylene castor oil, a hardened castor oil, a polyoxyethylene lanoline derivative, a polyoxyethylene beeswax derivative, and mixtures thereof.

2. The dental hydraulic temporary sealing material composition of claim 1, wherein the composition comprises from 30 to 70% by weight of (A) calcium sulfate.

3. The dental hydraulic temporary sealing material composition of claim 1, wherein the calcium sulfate is selected from the group consisting of α-type hemihydrate gypsum, β-type hemihydrate gypsum, gypsum dihydrate, anhydrous gypsum, and mixtures thereof.

4. The dental hydraulic temporary sealing material composition of claim 1, wherein the composition comprises from 10 to 30% by weight of (B) a vinyl acetate resin.

5. The dental hydraulic temporary sealing material composition of claim 1, wherein the vinyl acetate resin is selected from the group consisting of polyvinyl acetate, an ethylene vinyl acetate copolymer, a copolymer of vinyl acetate and vinyl chloride, a copolymer of vinyl acetate and acrylonitrile, a copolymer of vinyl ester and vinyl chloride, acrylic acid, maleic acid, fumaric acid, crotonic acid, a copolymer of these acids and ester, and mixtures thereof.

6. The dental hydraulic temporary sealing material composition of claim 1, wherein the composition comprises from 10 to 30% by weight of (C) an inorganic filler.

7. The dental hydraulic temporary sealing material composition of claim 1, wherein the inorganic filler is selected from the group consisting of zinc oxide, silica, silica fine powder, barium sulfate, zirconium oxide, titanium oxide, ytterbium fluoride, barium glass and aluminosilicate glass and mixtures thereof.

8. The dental hydraulic temporary sealing material composition of claim 1, wherein the composition comprises from 2 to 20% by weight of (D) at least one alcohol having a boiling point of 110° C. or more.

9. The dental hydraulic temporary sealing material composition of claim 1, wherein the at least one alcohol having a boiling point of 110° C. or more is selected from the group consisting of 1-butanol, t-butyl alcohol, 1-pentanol, isoamyl alcohol, s-amyl alcohol, t-amyl alcohol, 1-hexanol, 2-ethyl-1-butanol, 4-methyl-2-pentanol, isohexyl alcohol, methyl-1-pentanol, s-hexanol, 1-heptanol, isoheptyl alcohol, 2,3-dimethyl-1-pentanol, 1-octanol, 2-ethyl hexanol, isooctyl alcohol, 2-octanol, 3-octanol, 1-nonanol, isononyl alcohol, 3,5,5-trimethylhexanol, 1-decanol, isodecyl alcohol, 3,7-dimethyl-1-octanol, 1-dodecanol, isododecyl alcohol, higher alcohol having 6 to 11 carbons, ethylene glycol, triethylene glycol, tetraethylene glycol, polyethylene glycol, propylene glycol, 1,3 propanediol, dipropylene glycol, tripropylene glycol, polypropylene glycol, butanediol, 1,5-pentanediol, 2-methyl-2,4 pentanediol, 2,2,4-trimethyl-1,3-hexanediol, 2-ethyl-1,3-hexanediol, ethylene glycol monomethyl ether, ethylene glycol monovinyl ether, ethylene glycol monoethyl ether, ethylene glycol mono-n-propyl ether, ethylene glycol monoisopropyl ether, ethylene glycol mono-n-butyl ether, ethylene glycol monoisobutyl ether, ethylene glycol mono-t-butyl ether, ethylene glycol mono-2-methylpentyl ether, ethylene glycol mono-n-hexyl ether, ethylene glycol mono-2,4-hexadiene ether, ethylene glycol mono-2,6,8-trimethyl-4-nonyl ether, ethylene glycol monophenyl ether, ethylene glycol monomethylphenyl ether, ethylene glycol dimethyl ether, ethylene glycol diethyl ether, diethylene glycol monomethyl ether, diethylene glycol monoethyl ether, diethylene glycol mono-n-propyl ether, diethylene glycol mono-n-butyl ether, diethylene glycol monoisobutyl ether, diethylene glycol mono-n-hexyl ether, diethylene glycol dimethyl ether, diethylene glycol divinyl ether, diethylene glycol ethylvinyl ether, diethylene glycol monomethylphenyl ether, triethylene glycol monomethyl ether, triethylene glycol monoethyl ether, triethylene glycol mono-n-propyl ether, triethylene glycol monovinylethyl ether, tetraethylene glycol methyl ether, tetraethylene glycol butyl ether, tetraethylene glycol monophenyl ether, tetraethylene glycol diethyl ether, polyethylene glycol methyl ether, propylene glycol monomethyl ether, propylene glycol monoethyl ether, propylene glycol-n-monopropyl ether, propylene glycol monoisopropyl ether, propylene glycol mono-n-butyl ether, propylene glycol butoxyethyl ether, propylene glycol phenyl ether, dipropylene glycol monomethyl ether, dipropylene glycol monoethyl ether, dipropylene glycol mono-n-butyl ether, propylene glycol allyl ether, dipropylene glycol allyl ether, tripropylene glycol allyl ether, propylene glycol isobutyl ether, dipropylene glycol isobutyl ether, tripropylene glycol isobutyl ether, butylene glycol monomethyl ether, butylene glycol monoethyl ether, butylene glycol mono-n-butyl ether, and mixtures thereof.

10. The dental hydraulic temporary sealing material composition of claim 1, wherein the composition comprises from 0.1 to 2% by weight of (E) a nonionic surfactant.

11. The dental hydraulic temporary sealing material composition of claim 1, further comprising an additional components selected from the group consisting of a setting accelerator, an oil, an inorganic coloring agent, an organic coloring agent, an antibacterial material, a perfume, and mixtures thereof.

12. A dental hydraulic temporary sealing material composition consisting of:
A) 10 to 90% by weight of calcium sulfate;
B) 5 to 40% by weight of a vinyl acetate resin;
C) 1 to 40% by weight of an inorganic filler;
D) 1 to 30% by weight of an alcohol having a boiling point of 110° C. or more; and
E) 0.001 to 2% by weight of a nonionic surfactant, wherein the nonionic surfactant is selected from the group consisting of polyoxyethylene alkyl ether, polyoxyethylene alkylene ether, polyoxyethylene polyoxypropylene alkyl ether, polyoxyethylene alkylphenyl ether, sorbitan fatty acid ester, ethylene glycol fatty acid ester, polyethylene glycol fatty acid ester, propylene glycol fatty acid ester, pentaerythritol fatty acid ester polyoxyethylene sorbitan fatty acid ester, polyoxyethylene sorbital fatty acid ester, polyoxyethylene mannitan fatty acid ester, polyoxyethylene glycerine fatty acid ester, polyoxyethylene propylene glycol mono fatty acid, polyoxyethylene castor oil, a hardened castor oil, a polyoxyethylene lanoline derivative, a polyoxyethylene beeswax derivative, and mixtures thereof.

* * * * *